United States Patent
Tenney et al.

(10) Patent No.: US 9,392,965 B2
(45) Date of Patent: Jul. 19, 2016

(54) METHOD AND APPARATUS FOR DETERMINING A CHANGE IN TENSION OF A BODY SURFACE

(71) Applicant: Restoration Robotics, Inc., San Jose, CA (US)

(72) Inventors: John A. Tenney, Piedmont, CA (US); Mohan Bodduluri, Palo Alto, CA (US); Gabriele Zingaretti, Aptos, CA (US); Clifford A. Oostman, Jr., Hansville, WA (US)

(73) Assignee: Restoration Robotics, Inc., San Jose, CA (US)

( * ) Notice: Subject to any disclaimer, the term of this patent is extended or adjusted under 35 U.S.C. 154(b) by 581 days.

(21) Appl. No.: 13/804,320

(22) Filed: Mar. 14, 2013

(65) Prior Publication Data

US 2014/0276092 A1  Sep. 18, 2014

(51) Int. Cl.
*A61B 5/05* (2006.01)
*A61B 5/107* (2006.01)
*A61B 5/00* (2006.01)
*A61B 10/02* (2006.01)
*A61B 17/00* (2006.01)

(52) U.S. Cl.
CPC .............. *A61B 5/1072* (2013.01); *A61B 5/0059* (2013.01); *A61B 90/96* (2016.02); *A61B 10/02* (2013.01); *A61B 2017/00752* (2013.01); *A61B 2090/363* (2016.02)

(58) Field of Classification Search
CPC ........ A61B 19/22; A61B 19/50; A61B 19/56; A61B 19/5212; A61B 19/5225; A61B 2017/00752; A61B 2017/00969; A61B 2019/5227
See application file for complete search history.

(56) References Cited

U.S. PATENT DOCUMENTS

| | | |
|---|---|---|
| 1,550,403 A | 8/1925 | Turkus |
| 4,370,979 A | 2/1983 | Erickson |
| 4,434,791 A | 3/1984 | Darnell |
| 4,621,619 A | 11/1986 | Sharpe |
| 4,896,680 A | 1/1990 | Hirshowitz |
| 5,089,009 A | 2/1992 | Green |
| 5,441,540 A | 8/1995 | Kim |
| 5,449,374 A | 9/1995 | Dunn et al. |
| 5,486,196 A | 1/1996 | Hirshowitz et al. |
| 5,531,790 A | 7/1996 | Frechet et al. |
| 5,549,713 A | 8/1996 | Kim |

(Continued)

FOREIGN PATENT DOCUMENTS

| | | |
|---|---|---|
| DE | 4444130 | 6/1995 |
| WO | WO 01/03588 | 1/2001 |

(Continued)

*Primary Examiner* — Tse Chen
*Assistant Examiner* — Jason Ip
(74) *Attorney, Agent, or Firm* — Sharon Upham; Lena I. Vinitskaya (57) ABSTRACT

A method of detecting a change in tension of a body surface during a medical procedure is provided. In some embodiments the method may be carried out without additional invasive devices or procedures being required. In one example the methodology is applied when using any type of body surface tensioning device. The tensioning device comprises fiducials that are visible to an image acquisition device. In another example of an embodiment of the current application, the methodology may be applied by attaching fiducials directly to the body surface. The relative motion of the fiducials relative to one another may be utilized to determine a change in body surface tension.

23 Claims, 4 Drawing Sheets

(56) References Cited

U.S. PATENT DOCUMENTS

| | | | |
|---|---|---|---|
| 5,662,714 A | 9/1997 | Charvin et al. | |
| 5,759,193 A | 6/1998 | Burbank et al. | |
| 5,769,783 A | 6/1998 | Fowler | |
| 5,785,649 A | 7/1998 | Fowler | |
| 5,814,067 A | 9/1998 | Fleischmann | |
| 5,931,777 A | 8/1999 | Sava | |
| 5,964,697 A | 10/1999 | Fowler | |
| 5,971,920 A | 10/1999 | Nagel | |
| 5,972,021 A | 10/1999 | Huttner et al. | |
| 6,036,641 A | 3/2000 | Taylor et al. | |
| 6,120,436 A | 9/2000 | Anderson et al. | |
| 6,159,231 A | 12/2000 | Looney et al. | |
| 6,190,312 B1 | 2/2001 | Fowler | |
| 6,254,624 B1 | 7/2001 | Oddsen et al. | |
| 6,324,419 B1 * | 11/2001 | Guzelsu et al. | 600/476 |
| 6,445,943 B1 | 9/2002 | Ferre et al. | |
| 6,464,634 B1 | 10/2002 | Fraser | |
| 6,585,746 B2 | 7/2003 | Gildenberg | |
| 6,695,868 B2 | 2/2004 | Looney et al. | |
| 6,973,202 B2 | 12/2005 | Mostafavi | |
| 7,127,081 B1 | 10/2006 | Erdem | |
| 7,208,006 B2 | 4/2007 | Fleischmann | |
| 7,894,649 B2 | 2/2011 | Fu et al. | |
| 2003/0120298 A1 | 6/2003 | Gildenberg | |
| 2004/0049206 A1 | 3/2004 | Rassman | |
| 2006/0270909 A1 | 11/2006 | Davis et al. | |
| 2007/0021779 A1 | 1/2007 | Garvin et al. | |
| 2007/0049970 A1 | 3/2007 | Belef | |
| 2007/0078466 A1 | 4/2007 | Bodduluri et al. | |
| 2007/0282374 A1 | 12/2007 | Sogard et al. | |
| 2008/0002809 A1 | 1/2008 | Bodduluri | |
| 2008/0027484 A1 | 1/2008 | Lee et al. | |
| 2008/0114395 A1 | 5/2008 | Mathisen et al. | |
| 2008/0188921 A1 * | 8/2008 | Yamasaki et al. | 623/1.13 |
| 2008/0202200 A1 | 8/2008 | West | |
| 2010/0030260 A1 | 2/2010 | Fleischmann | |
| 2010/0080415 A1 | 4/2010 | Qureshi | |
| 2010/0166323 A1 | 7/2010 | Zhao et al. | |
| 2010/0191253 A1 | 7/2010 | Oostman et al. | |
| 2011/0152627 A1 | 6/2011 | Tannoury et al. | |
| 2011/0178533 A1 | 7/2011 | Oostman et al. | |
| 2012/0158019 A1 | 6/2012 | Tenney et al. | |
| 2014/0074115 A1 | 3/2014 | Oostman | |

FOREIGN PATENT DOCUMENTS

| | | |
|---|---|---|
| WO | WO 2006/132256 | 12/2006 |
| WO | WO 2008/107110 | 9/2008 |
| WO | WO 2008/156838 | 12/2008 |
| WO | WO 2009/155325 | 12/2009 |

* cited by examiner

METHOD AND APPARATUS FOR DETERMINING A CHANGE IN TENSION OF A BODY SURFACE

TECHNICAL FIELD

The present invention relates generally to medical devices and methods. More specifically, the invention relates to devices and methods for determining the change in surface tension of a body surface during a medical procedure, such as hair transplantation.

BACKGROUND

There are numerous surgical, cosmetic, therapeutic and dermatological procedures that involve maneuvering an area of skin. Hair transplantation is one of those procedures and it typically involves harvesting donor hair grafts, e.g. follicular units ("FUs"), from the "donor areas," and implanting them in a bald area ("recipient area"). Hair transplantation is very labor-intensive and complex procedure that requires skill and precision. During hair transplantation procedures, in order to apply tension to a skin surface in the area of hair harvesting or implantation, pressure is typically applied adjacent the target location using two fingers. Similar skin tensioning technique is used in various cosmetic and dermatological procedures other than hair transplantation.

SUMMARY

The present disclosure discloses a method and apparatus for determining a change in tension of a body surface. According to an aspect of the current application, a method of detecting a change in tension of a body surface or skin during a medical procedure is provided, the method comprising: determining a location of at least two fiducials, the fiducials operatively connected to a body surface on which a medical procedure is to be performed; determining a revised location of the at least two fiducials; and analyzing a change in location of the fiducials to determine if a change in tension of the body surface has occurred. The fiducials may be attached, for example, to a tensioning device that is placed on the body surface, or they may be placed directly on the body surface. Analyzing a change in location of the at least two fiducials may comprise determining an increase or a decrease in a distance between at least two of the at least two fiducials. Analyzing a change in location of the at least two fiducials may comprise determining a first area of a central opening based on a location of fiducials in a first image, and determining a second area of the central opening based on a location of fiducials in second image; and further comprise determining if the difference between the first and the second areas is equal to or above a predetermined value. The predetermined value may be an absolute threshold or a percentage of the first area. The method may be computer-implemented or computer-controlled. For example, a processor configured to perform one or more steps of the method may be used.

In various implementations, the method may further comprise providing notification that a change in tension of the body surface has occurred. Such notification may comprise a visual or audio notification, suggest that the user check for movement of the body surface grabbers on the tensioning device, or may prohibit performance of the medical procedure for example.

According to one embodiment of the current application, the method may be performed using a tensioning device comprising two laterally spaced members coupled to each other at their respective ends and defining a boundary around an opening within which the medical procedure is to be performed, wherein one of the at least two fiducials is disposed on a side of the opening opposite to the side of the other of the at least two fiducials, and wherein analyzing the change in location comprises determining a relative change in distance between the at least two fiducials.

According to another embodiment of the current application, the method may comprise determining the tension on a body surface at various stages of the procedure.

According to one implementation of the current application, the procedure may be a hair transplantation procedure such as a harvesting, site making or implantation procedure. The steps of determining the location and analyzing the change in the location may be repeated until all desired follicular units are harvested from or implanted a treatment area on the body surface.

According to another aspect of the current application, a system for detecting a change in tension of a body surface is provided. The system may comprise: an interface adapted to receive an image data containing images of a body surface; and a processor comprising a set of instructions for executing operations, the set of instructions including instruction for: recording a first location of at least two fiducials appearing in one or more images of the body surface; recording a revised location of at least two fiducials appearing in one or more images of the body surface; and analyzing a change in location of the fiducials to determine if a change in tension of the body surface has occurred. The system may further comprise a tool and the instructions further prohibit a tool from functioning. In some embodiments, the system may be a robotic system comprising a movable arm, and the tool may be operatively connected to the robotic arm. In some embodiments, the system may comprise an image acquisition device, which may be positioned in some embodiments on the movable arm.

Other and further objects, advantages and embodiments of the inventions of the present application will become apparent from the following detailed description when read in view of the accompanying figures.

BRIEF DESCRIPTION OF THE DRAWINGS

Features and advantages of the embodiments described herein will become appreciated as the same become better understood with reference to the specification, claims, and appended drawings wherein:

DETAILED DESCRIPTION

In the following Detailed Description, reference is made to the accompanying drawings that show, by way of illustration, some examples of embodiments in which the invention may be practiced. In this regard, directional terminology, such as "right," "left," "upper," "lower," "upwards," "downwards," "inwards," "outwards," "right," "left," etc., are used with reference to the orientation of the Figure(s) being described. Because components or embodiments of the present invention can be positioned or operated in a number of different orientations, the directional terminology is used for purposes of illustration and is in no way limiting. Other embodiments may be used, and structural or logical changes may be made, without departing from the scope of the present invention. The terms "operatively connected," "coupled," or "mounted," or "attached" as used herein, means directly or indirectly coupled, attached, or mounted through one or more intervening components.

As mentioned above, though the invention of the present application is particularly useful in providing devices and methods for harvesting (taking donor follicular units), "site making" (preparing a portion of the scalp for implantation) and implanting (placing harvested follicular units into the prepared site(s), it is not limited to hair transplantation. Although this description is made in reference to hair transplantation procedures, such as those performed, for example, on the scalp, various embodiments may be applied to various body surfaces and/or to other procedures. Other procedures where skin or any body surface is desired to be tensioned may benefit from the system and method of the inventions described herein. One example of applicability of the invention is in diagnostic skin imaging for cosmetic or other medical purposes. Other example of procedures include but are not limited to hair harvesting, hair implantation, biopsy procedures, tattoo placement and removal procedures, or other procedures requiring application and maintenance of some tension. For convenience of description, the following description will be discussed by example in reference to hair transplantation procedures. However, the description of hair transplantation procedures herein are for the purposes of illustration and example only, and should not be interpreted as limiting the scope of the invention as it is set forth in the claims.

In various procedures a body surface tensioner may be utilized to tension the body surface, for example the skin or a scalp, enabling the procedure to be performed. In some procedures it may be desirable that the body surface be tensioned such that a location on the tensioned skin may be accurately located, for example, to remove a follicular unit, or to continue application of a tattoo. Whatever the reason, it can be seen that a change in tension of the body surface may have undesirable consequences, should the procedure continue as if no change had occurred.

To apply tensile forces to the body surface, tensioning devices may comprise a frame having a contact surface that is or can be configured to lie substantially flush against the body surface. Example of skin tensioning devices can be found in U.S. Patent Publications 6007/0078466, 2010/0191253 and 20110178533, each reference incorporated by reference herein. A few of these skin tensioning devices that are particularly useful in hair transplantation procedures are illustrated in FIGS. 1a-1c.

Figure 1A:
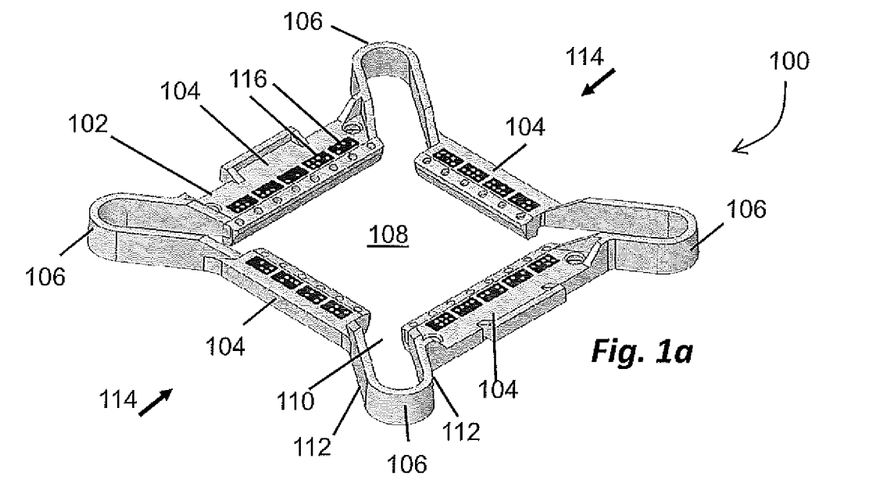
FIGS. 1a-1c illustrate examples of various skin tensioning devices.
Figure 1B:
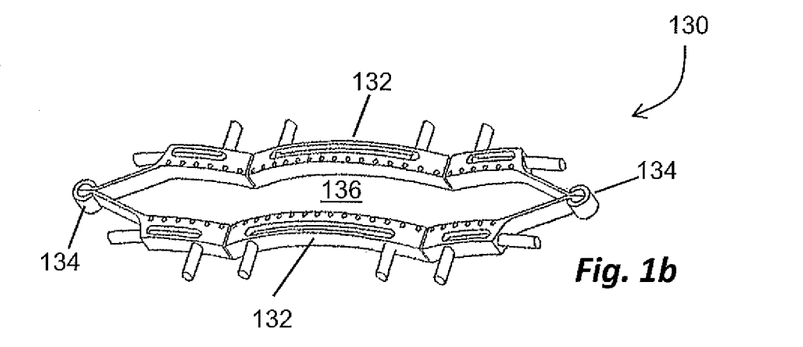
Figure 1C:
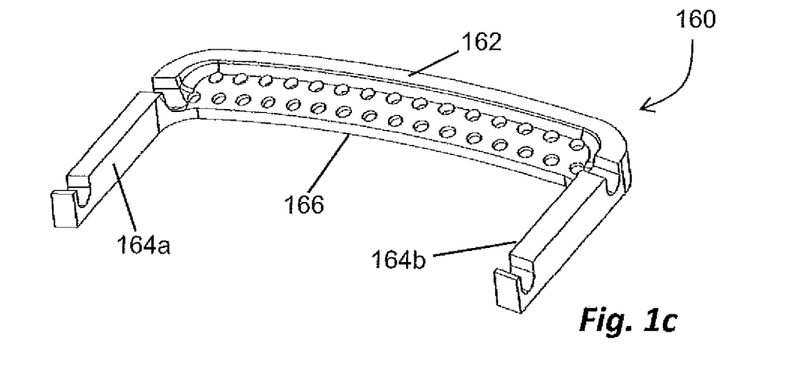

FIG. 1a illustrates a skin tensioning device 100 that has a closed-frame 102, which somewhat resembles a butterfly, and is termed "butterfly-style." The illustrated frame 102 is flexible and lies generally in a plane and preferably comprises a single element, typically molded material and is configured such that it may be compressed inward from a relaxed position. FIG. 1a shows the frame 102 in a relaxed configuration. The frame may comprise a resilient material, elastic in nature, or flexibility may be attained by the structure, shape, gaps, thicknesses, and/or material selection, for example, incorporated into parts of or into the entire frame. The flexible frame 102, in the example illustrated, includes four side sections 104 joined by four corners 106 that project diagonally outward therefrom. The four side sections 104 in this example are two generally parallel side sections perpendicular to two other generally parallel side sections, with the flexible corners extending generally diagonally outward from a center of a central opening 108 defined by the side sections 104. The frame comprises a body contacting surface that may be configured to conform to the body surface, and a upper surface, a surface that faces away from the body surface when in use. In this particular embodiment the procedure is performed in a central opening 108, inside the frame 102.

In the relaxed configuration of FIG. 1a, the gap 110 between each pair of beams 112 that from the corners 106, may be substantially constant. It should be noted that the user compresses the frame 102 by squeezing together two of the side sections 104, as indicated by the inward arrows 114, which also causes the perpendicular side sections to converge toward the center by virtue of their inward concavity. In this manner, the central opening 108 formed by the side sections 104 is smaller when the frame 102 is in its compressed state than in its relaxed state.

Each side section 104 may include a plurality of perforations for receiving one or more body surface grabbers, for example, barbs or microbarbs (not shown). The barbs provide an anchor for each of the side sections 104 on a skin surface. Although barbs are described herein as an example of ensuring good grip to the skin, other solutions that merely increase the coefficient of friction are contemplated as well. For instance, a frame with a contact surface having adhesive may be successfully utilized in conjunction with certain embodiments described herein. Another possibility is mating Velcro patches, with one temporarily adhered to the skin and one to at least a portion of an underside or bottom surface of the frame. Alternatively, suction could be utilized in certain embodiments. As such, the term "body surface grabber" as used herein encompasses various structures and ways of engaging the skin or body surface, such as by increasing the lateral resistance to movement of the frame across the skin surface in contrast to a smooth-bottomed surface. That is, "body surface grabber or grabbers" encompass barbs, microbarbs, suction, adhesives, Velcro, ribs, ridges, pins, etc., and even rough surface texture.

In a skin tensioning procedure, a user compresses the frame 202 into the configuration shown in FIG. 1a by squeezing the two opposed side sections 104 in the direction of arrows 114 (as mentioned, the other two sides also bow inwardly). As the opposing side sections 104 are arranged to be substantially square, eventually the four side sections 104 will be prevented from moving further when the corners of the side sections 104 meet each other. The four side sections 104 can then be pressed onto a skin surface surrounding an area of treatment such that the barbs (or similar skin grasper expedient) engage the skin surface. After releasing the frame 102, the four side sections 104 are biased outward by the resiliency of the corners 106, thus placing the skin surface in tension. Once the body surface is tensioned, for example, in the central opening 108, the user may commence the procedure to be performed on the tensioned body surface, for example, penetrating the body surface in the opening 108 of the frame 102 to dissect or implant a follicular unit. The opening 108 may form any suitable shape, such as but not limited to a square, a rectangle, a circle and a triangle.

Other forms of tensioning devices are illustrated in FIGS. 1b and 1c. FIG. 1b illustrates an elongated tensioning device. The tensioner 130 may comprise two laterally spaced elongate legs 132, which are coupled to each other at their respective ends 134 thereof, defining a boundary around an opening 136 within which a procedure can be carried out on a tensioned body surface. In alternative embodiments, any number of segments, or combinations thereof may be utilized to provide structures corresponding to the elongate legs 132. In some embodiments, the tensioning device 130 is configured to conform to and span any region of the body surface, body surfaces of various sizes, shapes and/or textures, thus allowing for customization in order to fit a variety of body surfaces. The tensioning device 130 also allows procedures to be performed on a region or an area comprising multiple curvatures, for example spanning from one side of a patient's head to the other.

In FIG. 1c, a perspective view of a body surface tensioning device 160 is illustrated, having a U-shaped frame 162. The frame 162 may comprise two arms 164a and 164b and a heel 166. The frame 162, or at least a portion of it, such as the heel 166, may have a plurality of perforations for receiving one or more body surface grabbers (not shown) as described above. When the at least one body surface grabber is engaged with the body surface, the tensioning device is configured to be moved by the displacement mechanism in substantially one direction to cause tension to be created in the body surface.

No matter what type of tensioning device is employed, if the frame or any part thereof, were to become partially or fully unattached from the body surface, it will be apparent that the tensioning device that was previously providing tension across the body surface, will no longer provide the same tension. A change in tension may be caused to change gradually, for example the barbs gradually bending, or more suddenly, for example by the barbs popping out of the body surface. Consequently, if the procedure was to continue to be performed while the required tension is no longer present, the tool used to perform the procedure may penetrate the body surface at an incorrect location, for example, implanting a follicular unit at the incorrect location, or may attempt to harvest a follicular unit that is no longer at that location, or harvest an incorrect follicular unit. In addition, since the body surface is no longer tensioned, or is only partially tensioned, the tool may penetrate the body surface in a different manner. For example, it may not penetrate the body surface at all, or if it does, it may penetrate to a different depth than desired, perhaps. The change in body tension may also reduce the quality of the extracted follicles, for example, they may be transected or otherwise damaged. In applications other than hair transplantation it may be also important to know if there is a change in the tension of the skin during a medical procedure to preserve the quality and integrity of the procedure.

In one aspect of the current application a method of detecting a change in tension of a body surface during a medical procedure is provided. In some embodiments of the current application, the method may be carried out without additional invasive devices or procedures being required. In one example of an embodiment of the current application, this methodology may be applied when using any type of body surface tensioning device that comprises fiducials or markers. In the embodiments implementing image guidance, the markers are configured to be visible to an image acquisition device, such as one or more cameras. In another example of an embodiment of the current application, the methodology may be applied by attaching fiducials to the body surface. The relative motion of the fiducials relative to one another may be utilized to determine a change in body surface tension. Utilization of such methodologies enable changes in the body surface tension to be determined such that the procedures being performed can be performed in an effective manner.

Whether on a tensioning device, or attached directly to the body surface, the fiducials are identifiable in a field of view of an imaging device. Fiducials are artificial markers and can take many forms. The fiducials may be disposed, for example, around a treatment area, an area in which the medical procedure is to be performed. Referring back to FIG. 1a, the frame 102 of the tensioning device may also hold any suitable number of fiducial markers 116, such as between 1 fiducial and 100 fiducials. On tensioning devices such as those illustrated in FIG. 1a, with a central opening 108, the fiducials may be disposed on one or more sides of the central opening 108. In this particular example there are four sets of fiducials, disposed on all four side sections 104 of the frame 102. These fiducials 116 are visible under image guidance and may be attached to the upper surface of the frame 102, and may additionally provide a convenient reference framework for aiming a tool, such as a follicular unit removal or implant tool, particularly when an automated and/or computer-assisted procedure is performed in the central opening 108. In some embodiments, all the fiducial 116 are substantially the same. In other embodiments one or more of the fiducials 116 are distinguishable from others. In alternative embodiments, all of the fiducials 116 are distinguishable from each other. The fiducials 116 serve as objects, or reference marks in a field of view of an image acquisition device. These fiducials 116, when viewed in an image, can be recognized in the image, and may be individually recognizable from each other in subsequent images. Fiducials 116 may be physically identified by an imaging device in either two or three dimensions. Known techniques for recording the location of such visual markers include using coded targets such as data-matrix targets, normalized grayscale correlation, or pattern-based recognition. The fiducials may comprise a 1-D bar code, a 2-D data matrix code, known markings such as alphanumeric characters, a series of dots, a series of bars, or any other type of unique identifier or custom scheme.

Figure 2:
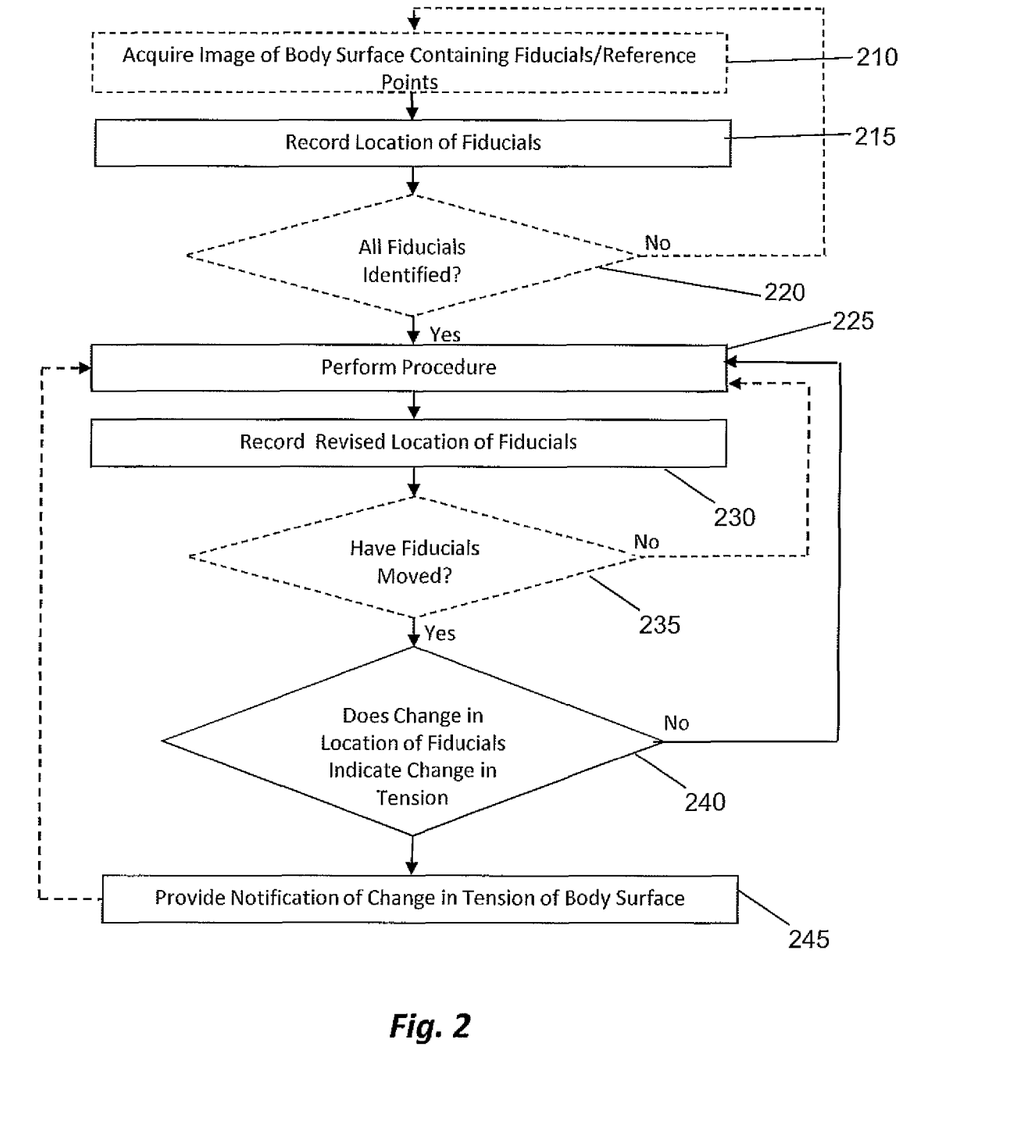
FIG. 2 is a block diagram illustrating one example of a method for performing determining if there has been a change in the tension of a body surface.

FIG. 2 is a block diagram illustrating an example of a methodology according to one aspect of the invention, of using image guidance and fiducials to detect a change in tension in a body surface. At step 210 (which may be a preliminary step, represented by a dotted line), one or more images of the body surface with one or more reference points, such as a plurality of fiducials, may be obtained, for example, using optical sensing techniques and/or an image acquisition device. This may be accomplished by any technique known in the art. For example, in some embodiments, an image acquisition device may be attached to a robotic arm, and the robotic arm with the attached image acquisition device may be positioned so that the harvesting Or implantation region is in focus for the cameras. In other embodiments, the image acquisition device may be incorporated into the automated (e.g., robotic) system but not attached to the robotic arm. Alternatively, in further embodiments, the image acquisition device could be a device separate from the robotic system. The image acquisition device may comprise one or more cameras, or may comprise stereo imaging.

At step 215, a processor or an image processor, processes and records a location (and optionally an identity) of each of the fiducials in a frame of reference of an image acquisition device (e.g., in a camera field of view). Such initial recoding of fiducials could be referred to as "fiducial registration" and may comprise location coordinates in 2D or 3-D. The fiducials could be recorded in various coordinate systems, for example, in a fixed "world" coordinate system. It will be understood by those of ordinary skill in the art that the image processor for use with the present application may be programmed and configured to perform various known image processing techniques, for example, segmentation, edge detection, object recognition and selection. These techniques are generally known and do not need to be separately described here. In this manner, the registration of fiducials can be processed.

There may be situations in which an image acquired by the image acquisition device includes only a subset of the fiducials, such that images of additional fiducials are needed, step 220 optionally provides for acquiring additional images as needed, for example, including other subsets of the fiducials, until all fiducials have been identified. This may be necessary, for example, when a structure such as that illustrated in FIG. 1b is utilized.

At this stage, step 225, the procedure may be performed. When reference is made to a "procedure" performed on a body surface, this is meant to refer generally to any process performed on a body surface, including a portion of a procedure or a complete procedure.

Throughout the procedure periodically, at times that may be specified by the processor, an image processor or the user, subsequent images are acquired and processed, such that an identity and a revised location of each of the fiducials is once again recorded in a frame of reference of an image acquisition device (e.g., in a camera field of view), step 230. Alternatively, the revised location of the fiducials may be acquired and processed after each or a specified number of events during a procedure, for example, after harvesting each follicular unit. In some instances the location of the fiducials will be substantially the same as for the previous processed location, in other instances it may be revised, a different location to that previously processed.

Optionally, at step 235 of the methodology, the processor determines whether one or more of the fiducials has moved. In some embodiments, the processor may determine whether one or more of the fiducials has moved relative to one or more other fiducials. If the revised locations/positions of the fiducials are substantially the same as the previous locations/positions, or the relative positions/location of the fiducials relative to one another has not substantially changed, the procedure may continue to be performed. If, however, a change in location of one or more fiducials is determined to have occurred, or the location of the fiducials relative to one another has changed, the processor may then in step 240 determine whether the detected change represents a change in body surface tension. Alternatively, this step 235 may be omitted, and step 240 carried out.

Having acquired the revised locations of the fiducials, and with the knowledge of the original (or previous) locations of the fiducials, it is determined in step 240 if the change in location for at least some or all of the fiducials is indicative of a change in body surface tension. In one example of an embodiment of the current application, the current and previous locations of a fiducial are utilized to determine if the distance between two or more fiducials has changed. In another example of an embodiment of the current application, the current and previous locations of a fiducial are utilized to determine if the central opening within the tensioning device has changed in size, becoming larger or smaller. Some examples of various methodologies as to how this step may be achieved will be described below.

If it is determined in step 240 that a change in body surface tension has occurred, a notification to that effect may be provided in step 245. Whether the medical procedure is being performed by the surgeon is a manual or a substantially automated or computer-assisted procedure, this notification may be provided by activating a notification output. The notification may be provided to the user via a hand-held device, a monitor, voice command, or any other appropriate technique, whether that be for example auditory, visual and/or some other sensual indication to the surgeon that a change in tension of the body surface has been determined. In the case of a substantially automated procedure, perhaps incorporating the use of a computer system, notification may be provided by illuminating a warning indicator on a user console, or terminating the procedure. Though it will be appreciated that the system may be programmed to stop in certain instances, for example, at a point when the needle is retracted from the patient's body surface. If the motion is not indicative of a change in body surface tension, the procedure may continue.

Having been notified that a change in the tension of the body surface has been determined, at this point the tension of the body surface may be modified, for example by a user, in a manner that enables the medical procedure to be continued. The notification may suggest that the user check whether perhaps the body surface grabbers have moved, become bent or popped out from the body surface. Once a modification has been carried out to remedy the problem, the user may then re-start the procedure, enabling the procedure to be executed on the once again tensioned body surface. It will be apparent that notification alone may not necessitate modification of the body surface tension, and that the user may opt to allow the procedure to continue despite the change in body surface tension. In some embodiments the user may only terminate the procedure if movement of the fiducials is above a predetermined threshold value. In other embodiments the user may be able to modify the body surface tension without terminating the procedure, on the fly, so to speak.

Figure 3:
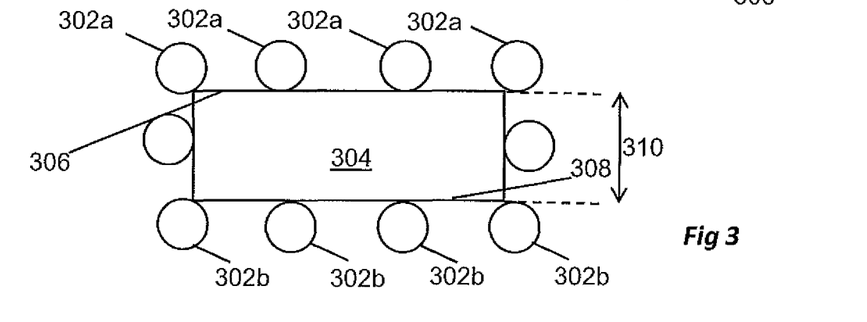
FIG. 3 illustrates an example of how fiducials may be used to determine a change in body surface tension.

FIG. 3 is schematic illustration of fiducials on a tensioning device (not shown), the tensioning device being attached to a patient, and is for illustrative purposes only, so that the methods of the current application that are described herein can be more readily understood. However any of the features described in reference to FIG. 3, however, may be applied to any of the embodiments described throughout the application. FIG. 3 illustrates the location of ten fiducials, as imaged by an image acquisition device in step 215. These fiducials are disposed on a tensioning device 300 (not shown), similar to any of those described above. In this particular example, it can be seen that there are four fiducials disposed on the upper portion of the frame and four fiducials disposed on the lower portion of the frame. The side portions each have three fiducials, though two of them are common with those located on the upper and lower portions of the frame. The above-mentioned numbers and locations of the fiducials are strictly for illustrative purposes, and any other number, location and configuration of the fiducials may be used. As indicated, a first set of fiducials 302a is disposed on one side of the central opening 304, and a second set of fiducials 302b is disposed on the other side of the central opening 304. Having registered the initial location of the fiducials, in one aspect of an embodiment of the current application, the processing unit processes a line of best fit tangential to the fiducials found on at least two sides of the tensioning device. For example, a line 306 represents tangential to the four fiducials on the upper portion of the tensioning device and a line 308 represents tangential to the four fiducials on the lower portion of the tensioning device. Alternatively, or in addition, a line (in a vertical direction) tangential to the three fiducials on the right-hand side portion of the tensioning device may be determined and a line tangential to the three fiducials on the left-hand side portion of the tensioning device may be determined. The tangential lines 306 and 308 are illustrated as being on the side of the fiducials that is closest to the central opening 304, however they could equally be on the side of the fiducials that are furthest from the central opening 304. In alternative example, the lines could be such that they go through the centroids of the four fiducials 302a on the upper portion of the tensioning device and the four fiducials 302b on the lower portion of the tensioning device, or through the centroids of the three fiducials on the right-hand side portion of the tensioning device and the three fiducials on the left-hand side portion of the tensioning device. In other embodiments, any fixed relationship, for example, between a line and the fiducials, whether it be through the center of the fiducial or offset from the center of the fiducial, will suffice. Having executed this step, the processor may determine the distance 310 between the two lines. It will be apparent that the two tangential lines 306 and 308 may not be parallel to one another, and as such the distance 310 determined may comprise locating the points which define the smallest distance between the two tangential lines 306 and 308, locating the point which define the largest distance between the two tangential lines 306 and 308, or taking the averaged between points at which there is the smallest and largest distance between the two tangential lines 306 and 308, or other appropriate statistical approach.

In another example, rather than utilize tangential lines 306 and 308, a determination of a change in distance between a fiducial on one side of the central opening 304, and a fiducial on the other side of the central opening 304, may suffice. In another example, the change in distances between multiple pairs of fiducials may be determined. For example, the lower, upper, or average value of distances corresponding to the multiple pairs and changes in such distances may provide a means for determining if the user should be notified that a change in the location of fiducials representative of a change in the tension of a body surface has occurred.

Figure 4:
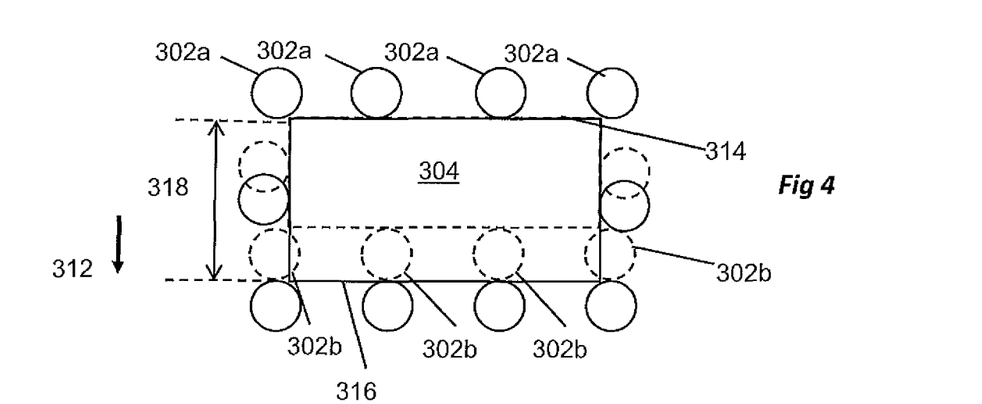
FIG. 4 illustrates another example of how the movement of the fiducials may be used to determine a change in body surface tension.

FIG. 4 represents schematically the location of the same ten fiducials that are imaged by the image acquisition device at some point later in time. In this particular example, it can be seen that the current location of the fiducials 302a on the upper portion of the tensioning device are substantially the same as the previous location of the fiducials on the upper portion of the tensioning device. However it can be seen that the some of the fiducials, indicated by the full lines, are in a different location that the previous image. The broken lines represent the previous locations for the fiducials whose locations have moved. As indicated, the four fiducials 302b on the lower edge of the tensioning device have moved downwards, in the direction indicated by the arrow 312. In addition, the two fiducials on the sides of the tensioning device have also moved downwards in the direction indicated by the arrow 312. Let us assume, for sake of argument, that in this particular example, the processor is basing its calculations on the location of the fiducials on the upper and lower portions of the tensioning device. The processor determines a line 314 tangential to the four fiducials on the upper portion of the tensioning device and a line 316 tangential to the four fiducials on the lower portion of the tensioning device. The processor is consequently able to determine the distance 318 between the two lines 314 and 316. As illustrated, the lines have moved further apart, and the central opening has become larger. It can therefore be determined that there may have been a change in tension in the patient's body surface. This change in tension may be due to the barbs bending, becoming partially or fully removed from the body surface during the procedure, or to perhaps the procedure itself causing the body surface tension to change. No matter what the cause, the user may be notified that such a change has occurred. In some embodiments, a small change may not be of concern, but a change above a predetermined threshold value may be detrimental to the outcome of the medical procedure being performed. Therefore, in some instances, the user may only be notified if the change is above a predetermined threshold value or a percentage, for example, of the initial distance 310.

Figure 5:
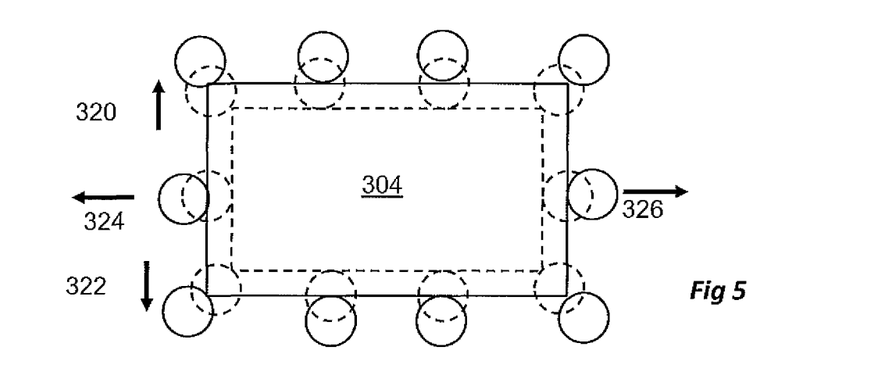
FIG. 5 illustrates yet another example of how the movement of the fiducials may be used to determine change in body surface tension.

FIG. 5 represents schematically another example of ten fiducials that are imaged by the image acquisition device. The dotted lines indicate the location of the fiducials and the tangential lines at an initial (or previous) point in time. The solid lines indicate the revised location of the fiducials and the revised tangential lines at a subsequent point in time. In this particular example, it can be seen that the current location of the fiducials on the upper portion of the tensioning device have moved in an upwards direction 320, while the fiducials on the lower portion of the tensioning device have moved in a downwards direction 322, and each of the side fiducials has moved outwards, in directions 324 and 326. In some embodiments, rather than determining a change in distance between fiducials disposed on one side of a tensioning device and another, the change in area of the central region 304 may be determined.

In order to utilize this process, in reference to the illustrated example, the processor may compute the area of the rectangle represented by a line tangential to the four fiducials on the upper portion of the tensioning device, a line tangential to the four fiducials on the lower portion of the tensioning device, a line tangential to the three fiducials on the right-hand side portion of the tensioning device, and a line tangential to the three fiducials on the left-hand side portion of the tensioning device. This computation is carried out with respect to the schematic illustrated in FIG. 3, at a "previous" time. At a subsequent time, the processor once again computes the area of the rectangle represented by the revised line tangential to the four fiducials on the upper portion of the tensioning device, the revised line tangential to the four fiducials on the lower portion of the tensioning device, the revised line tangential to the three fiducials on the right-hand side portion of the tensioning device, and the revised line tangential to the three fiducials on the left-hand side portion of the tensioning device. As described previously, the user may be notified that such a change has occurred. In some embodiments, a small change may not be of concern, but a change above a predetermined threshold value, for example, a predetermined minimum percentage of the initial area, may be detrimental to the outcome of the medical procedure being performed. Therefore, in some instances, the user may only be notified if the change is above a predetermined threshold value or percentage.

In the above-described examples, the fiducials have been disposed such that they surround a tensioned body surface on which a procedure is to be performed. Also, fiducials positioned on opposing sides of the tensioned body surface may be utilized to determine if there is a change in tension. With respect to tensioning devices of the type illustrated in FIG. 1c, if desired, in some embodiments a strip of additional fiducials may be placed, for example, on the patient's body surface, opposite fiducials placed on the tensioning device. Any change in distances between fiducials located on the tensioning device and on the strip may be used to calculate a change in tension.

In the example described above, the tensioning device has been described as expanding due to the change in tension in the body surface. However, depending upon the configuration of the tensioning device, in some embodiments that tensioning device may contract due to a change in tension. In addition, the area in tension may be for example the area defined by the central opening 304, or be the area outside the opening. The current application is intended to include all embodiments in which a change in tension is determined in the body surface based on a change in location or relative location of fiducials.

In some embodiments of the current application, the fiducials may be disposed at any number of locations, at various locations with respect to each other, and/or with respect to the tensioned body surface on which a procedure is to be performed. For example, a tensioning device may comprise two substantially parallel flexible, elastic members, coupled to each other at their respective ends, with fiducials disposed on either or both of the members. In some embodiments, the members may be elongated. To use such a device, a user may stretch/compress the elastic members before pressing them onto the skin surface on which a procedure is to be performed, such that the barbs (or similar skin grasper expedient) engage the skin surface. In this "tensioned" position, one of the fiducials on one of the elongated members (e.g., a first fiducial) may be a certain distance apart from an adjacent fiducial on the same elongated member. In this tensioned position, the user may commence the procedure to be performed on the tensioned body surface. If the tension in the body surface were to subsequently change (or one of the barbs to come loose), the elongated members may, for example, contract/expand, and as a consequence, the distances between one or more fiducials may change. For example, the first fiducial may be closer/further in distance to its adjacent fiducial than it was in the starting position. The revised locations of the fiducials, and the change in distance relative to one another, thereby indicating that there has been a change in body surface tension. It will be apparent that this is just one example of many configurations that may be utilized to implement the teachings of the current application. Fiducials may also, for example, be disposed on two substantially orthogonal members of a tensioning device, and be utilized in a similar manner.

It will also be apparent that in another aspect of the current application the fiducials may be disposed directly on a patient's body surface and provide indication about the change in tension. Skin is naturally movable and elastic in nature, having the ability to stretch when a force is applied to it, and then go back to normal once the stretching force is removed. Therefore, if fiducials are placed directly on the skin, when skin is put under tension (whether stretching it manually or by use of a tensioning device), the distance and/or relative position between several fiducials placed on the skin will change. According to one example, optionally the initial location of, for example, two fiducials on the skin before any tension is applied may be recorded. The revised location of the two fiducials may then be recorded again when a desired level of tension is present. During procedure, should the relative distance between the two fiducials change, this will indicate that there may have been a change in tension in the body surface. The actual tension may also be measured, for example, as described below.

In yet a further aspect of the current application, utilization of a tensioning device having known elastic modulus, may also enable the user and/or processor to estimate and/or evaluate an actual measurement of the change in tension of the body surface, based on the distance change in the fiducial location and the elastic modulus of the tensioning device. This estimation may take into account the varying elastic nature of the patient's body surface, and/or the area being tensioned. For example, in one embodiment of this aspect of the application, one may assume that the tensioning device functions in a similar manner to a spring, and therefore the force F needed to extend or compress the "spring" by some distance X is proportional to that distance, $F=kX$ where k is a constant characteristic of the spring, for example, the elastic modulus. In this manner, by experimentation or by use of a look-up table (giving a relationship between displacement and force for a specific elastic modulus), one can determine the force F exerted by the tensioner from the measured compression X. Assuming that the force F is distributed equally against along each side of the tensioner, for example via the barbs attaching to the body surface, one can therefore estimate the tension applied to the skin. In this manner, fiducials may be attached to the tensioner, their locations recorded before a procedure is performed, and a starting tension value estimated. If the revised location of the fiducial is subsequently recorded during the procedure, as described earlier, measurement of the relative location of the fiducials with respect to one another may indicate a change in tension of the body surface. In addition, by measuring the actual change in distance between the two fiducials, for example, one is able to estimate the change in tension applied the body surface. A processor may be configured to further notify the user if a predetermined threshold with respect to the change in tension has been exceeded.

No matter which tensioning device is selected for use, as indicated above, fiducials, in addition to being utilized to indicate if the tension in a body surface may have changed during a medical procedure, may also be utilized as reference marks for the positioning of a tool, for example, to harvest or implant a follicular unit or to perform other procedure.

Embodiments of the methods of the present invention may be implemented using computer software, firmware or hardware. Various programming languages and operating systems may be used to implement the present invention.

Figure 6:
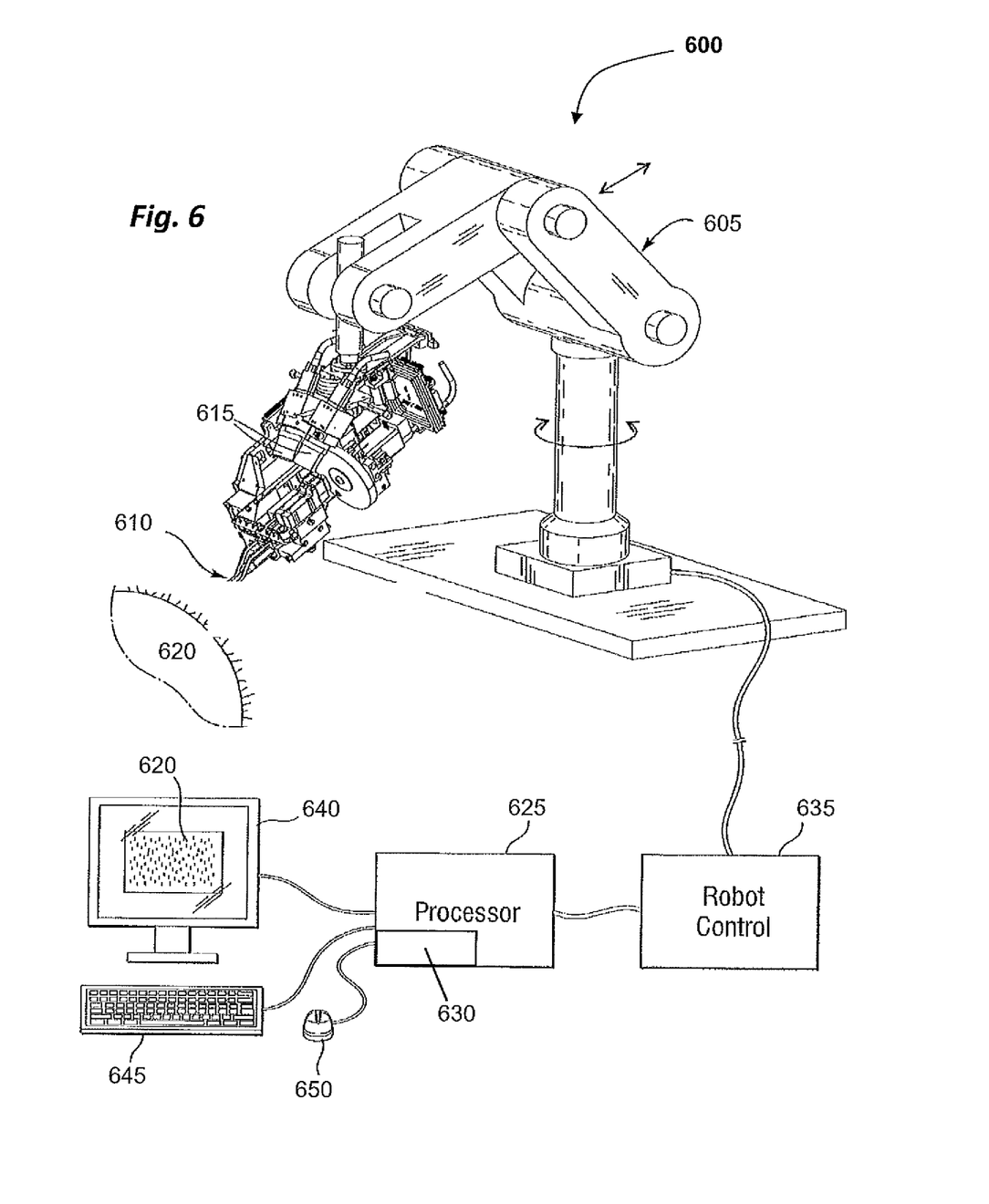
FIG. 6 is a schematic representation of an example of a robotic system that may be used in implementing various embodiments of the present application.

Referring now to FIG. 6 an example of a system that may be used to implement various embodiments of the method described herein is schematically shown. FIG. 6 is a schematic perspective view of an example of a robotic system 600 for hair harvesting (and/or implantation). The system 600 includes a robotic arm 605 to which is coupled a tool 610. Various motors and other movement devices may be incorporated to enable fine movements of an operating tip of the tool 610 in multiple directions. The robotic system 600 further includes at least one image acquisition device 615, which is described in more detail below. The image acquisition device may be mounted in a fixed position, or it may be coupled (directly or indirectly) to a robotic arm 605 or other controllable motion device. The operating tip of the tool 610 is shown positioned over a body surface 620, in this case a part of the patient scalp having hair follicles thereon. In some embodiments, an image acquisition device may be provided separately and not included in the system. In those embodiments, an interface may be provided that allows various other components or modules of the system, such as image processing component, to interact with the separate image acquisition device.

A processor 625 may include an image processor 630 for processing images obtained from the image acquisition device 615. The image processor 630 may be a separate device, or it may be incorporated as a part of the processor 625. The processor 625 may also instruct the various movement devices of the robotic arm 605, including the tool 610 that may be operatively connected to the robotic arm. The processor 625 may act, for example, through a controller 635. The controller 635 may be operatively coupled to the robotic arm and configured to control the motion of the robotic arm, including the motion based on the images or data acquired by the image acquisition device. Alternatively, controller 635 may be incorporated as a part of the processor 625, so that all processing and controls of all movements of all the tools, the robotic arm and any other moveable parts of the assembly, including those based on the images or data acquired by the image acquisition device, are concentrated in one place. The system 600 may further comprise a monitor 640, keyboard 645, and mouse 650. A magnified image of the body surface 620 can be seen on the monitor 640. In addition, the system 600 may include other tools, devices and components, for example, those useful in harvesting, and/or implantation of the hair follicles, or in hair treatment planning. The system further includes an interface adapted to receive an image data, various parts of the system allow an operator to monitor conditions and provide instructions, as needed. The interface may also include an indicator or other such means to notify the user of a change in the patient's body surface tension. The processor 625 may interact with the imaging device 615 via the interface (not shown). The interface may include hardware ports, cables, leads, and other data transmission means, or it may include a computer program.

Some non-limiting examples of the image acquisition device 615 include one or more cameras, such as any commercially available cameras. Of course, various image capture devices (or imaging devices) or optical sensors could be used with any of the embodiments of the systems and methods described herein. For example, the imaging device may be one or more cameras, such as any commercially available cameras. While stereo or multi-view imaging devices are typically very useful in the system 600, it is not necessary to employ such geometries or configurations in all embodiments. Likewise, although it is preferred that the image acquisition device be a digital device, it is not required. For example, the image acquisition device could be an analog TV camera that acquires an initial image, which is then processed into a digital image (for example, via an analog-to-digital device such as a commercial-off-the-shelf frame grabber).

The image acquisition device 615 may be coupled to a processing system, shown incorporated in the processor 625 in FIG. 6, to control the imaging operation and process image data. The processor 625 may comprise any suitable device programmed and configured to perform various methods as described herein, for example, including methods directed to determining a change of tension in a treatment area in various procedures, including without limitation hair transplantation. For example, the processor 625 may include a set of instructions for executing any one or more of the following operations: processing one or more images of a body surface to determine locations of a plurality of distinctive fiducials appearing in the one or more images; processing one or more images of a body surface to determine revised locations of a plurality of distinctive fiducials appearing in the one or more images; determining a change in the position or distance of the at least two fiducials with respect to each other, the fiducials may be attached to a body surface on which a medical procedure is to be performed (either directly or through a device placed on the body, such as skin tensioner); and analyzing the determined change in the position/motion of the fiducials to determine if a change in tension of the body surface has occurred. The image processor may be further configured to provide notification to a user about the change of tension, and in some embodiments calculate such change in tension. The image processor may be programmed and configured to perform various known image processing techniques, for example, segmentation, edge detection, object recognition and selection.

By way of example, and not limitation, a suitable processor or image processor may be a digital processing system that includes one or more processors or other type(s) of device. For example, a processor (image processor) may be a controller or any type of personal computer ("PC"). Alternatively, the processor (image processor) may comprise an Application Specific Integrated Circuit (ASIC) or Field Programmable Gate Array (FPGA). The processor may also include memory, storage devices, and other components generally known in the art (and thus not described in detail herein). The above-described processor could be used in conjunction with various partially automated and fully automated (including robotic) hair transplantation and treatment systems and devices, including but not limited to systems for hair harvesting, or hair transplantation.

The foregoing description, related to FIG. 6, is merely one example of a potential system or apparatus that could be used with the methods and devices discussed in the present application. In alternative embodiments, any other suitable image-guided systems may be used. Moreover, the described methodology may be implemented in manually performed or partially automated procedures. For example, the fiducials may be placed directly on the skin or natural features, such as anatomical landmarks or skin markings, may be used as fiducials in some procedures, and used in procedures discussed herein.

Although the various examples and embodiments are often described herein with relation to hair transplantation, in various alternative embodiments, the various concepts discussed can be applied more broadly to other appropriate applications. Additionally, although the methods described herein are especially suited for use with image-guided systems (including robotic systems) for hair harvesting and/or implanting, they can be applied to other computer-implemented or image-guided applications. For example, devices and methods described herein may be used in various ablation procedures, biopsy procedures, spinal procedures, dermatological procedures (e.g., tattooing or tattoo removal, or treating various dermatological conditions, such as skin cancers) and other procedures that could benefit from the locator device described herein. Therefore, the examples provided herein are for the purposes of illustration and example only, and this description is not intended to be exhaustive or limiting.

Numerous changes, variations, and substitutions will occur to those skilled in the art without departing from the invention. Various alternatives to the embodiments of the invention described herein may be employed in practicing the invention. It should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Similarly, the devices and methods described herein may be used in manual, semi-automated and fully automated procedures, including image-guided and robotic procedures.

What is claimed is:

1. A method of detecting a change in tension of a body surface during a medical procedure, the method comprising:
    determining a location of at least two fiducials in a first image, the fiducials operatively connected to a tensioning device, the tensioning device having a central opening with the at least two fiducials disposed around the central opening, and the tensioning device operatively connected to a body surface on which a medical procedure is to be performed;

determining a first area of the central in the first image;

determining a second area of the central opening in a second image; and determining if a difference between the first and the second area is equal to or above a predetermined value, wherein the first and second areas are determined by computing a line tangential to the fiducials on an upper portion of the tensioning device, a line tangential to the fiducials on a lower portion of the tensioning device, a line tangential to the fiducials on a right-hand side of the tensioning device and a line tangential to the fiducials on a left-hand side of the tensioning device.

2. The method of claim 1, wherein the tensioning device comprises a flexible frame and the central opening forms a variety of shapes.

3. The method of claim 1, wherein determining the location comprises optically sensing.

4. The method of claim 1, wherein an area in tension comprises the central opening, or an area outside the central opening.

5. The method of claim 1, further comprising providing notification that a change in tension of the body surface has occurred.

6. The method of claim 5, wherein the tensioning device comprises body surface grabbers which engage the body surface at least when the body surface is in tension, and the notification suggests that the user check whether the body surface grabbers have moved.

7. The method of claim 1, further comprising prohibiting performance of the medical procedure if it is determined that a change in tension above or below a pre-determined threshold has occurred or allowing to proceed with the medical procedure if a change in tension is within a pre-determined threshold.

8. The method of claim 1, wherein the tensioning device comprises two laterally spaced apart members coupled to each other at their respective ends and defining a boundary around the central opening within which the medical procedure is to be performed, wherein one of the at least two fiducials is disposed on one side of the opening and the other of the at least two fiducials is disposed on an opposite side of the opening, and wherein the method comprises determining a relative change in distance between the at least two fiducials.

9. The method of claim 1, the method comprising locating points which define a smallest distance between at least two tangential lines of best tangential fit, a largest distance between the at least two tangential lines of best tangential fit, or an average between points at which there is the smallest and the largest distance between the at least two tangential lines of best tangential fit.

10. The method of claim 1, wherein the best fit tangential line is determined based on a side of a fiducial that is closest to the central opening, a side of a fiducial that is furthest from the central opening, or goes through centroids of the at least two fiducials.

11. The method of claim 1, wherein the predetermined value is an absolute threshold or a percentage of the first area.

12. The method of claim 1 wherein the first image is taken at a first moment in time, and the second image is taken at a second moment in time.

13. The method of claim 1, wherein one or more steps of the method are computer controlled.

14. The method of claim 1 further comprising estimating an actual measurement of change in tension of the body surface based on an elastic modulus of the tensioning device.

15. The method of claim 1, wherein the medical procedure is a hair transplantation procedure, and the method further comprises repeating the steps of determining the first and second areas, and determining if the difference between the first and the second area is equal to or above a predetermined value until all desired follicular units are harvested from or implanted into a treatment area on the body surface.

16. A system for detecting a change in tension of a body surface, comprising:

a user interface configured to receive image data containing images of a body surface; and a processor comprising a set of instructions for executing operations, the set of instructions including instruction for:

recording a location of at least two fiducials appearing in a first image of the body surface, the fiducials operatively connected to a tensioning device, the tensioning device having a central opening with the at least two fiducials disposed around the central opening, and the tensioning device operatively connected to a body surface on which a medical procedure is to be performed;

computing a first area of the central opening in the first image;

recording a revised location of at least two fiducials appearing in a second image of the body surface;

computing a second area of the central opening in the second image; and determining if a difference between the first and the second area is equal to or above a predetermined value;

wherein the first and second areas are determined by computing a line tangential to the fiducials on an upper portion of the tensioning device, a line tangential to the fiducials on a lower portion of the tensioning device, a line tangential to the fiducials on a right-hand side of the tensioning device and a line tangential to the fiducials on a left-hand side of the tensioning device.

17. The system of claim 16, wherein the set of instructions further comprises providing notification that a change in tension of the body surface has occurred.

18. The system of claim 17, wherein the notification is provided via a hand-held device, a monitor, voice command, or any other technique, and wherein notification comprises a visual or audio notification.

19. The system of claim 16, wherein the set of instructions further comprises prohibiting a tool from functioning.

20. The system of claim 16, wherein the system comprises a hair transplantation system, and the tool comprises a hair harvesting tool and/or a hair implantation tool.

21. The system of claim 16, further comprising an image acquisition device.

22. The method of claim 7, wherein the medical procedure comprises use of a needle, and wherein the method comprises prohibiting performance of the medical procedure at a point when the needle is retracted from the body surface.

23. The system of claim 16, wherein the central opening forms a square or a rectangle and the fiducials are additionally utilized as reference marks for positioning of a tool used to perform the procedure.

* * * * *